US00PP13290P2

(12) United States Plant Patent
Heims

(10) Patent No.: US PP13,290 P2
(45) Date of Patent: Nov. 26, 2002

(54) PULMONARIA PLANT NAMED 'SILVER SHIMMERS'

(75) Inventor: Daniel M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/989,926

(22) Filed: Nov. 20, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A. Para
(74) *Attorney, Agent, or Firm*—Klarquist Sparkman, LLP

(57) ABSTRACT

A new and distinct hybrid of Pulmonaria plant characterized by silver leaves with undulate margins and large, blue violet flowers.

2 Drawing Sheets

BOTANICAL CLASSIFICATION

Pulmonaria hybrid.

VARIETY DENOMINATION

'Silver Shimmers'.

BACKGROUND OF THE INVENTION

The present invention relates to a new and distinct hybrid of Pulmonaria, of the family Boraginaceae, which originated as an open-pollinated cross between unknown parents in a breeding program carried out in Canby, Oreg. This is known to be an outcross because Pulmonaria does not normally self-pollinate. Due to the fact that the instant plant and parent plants are interspecific hybrids from several generations of interbreeding and selecting, no species designations are given.

SUMMARY OF THE INVENTION

This new plant is characterized by:

1) Highly silvered foliage;
2) Undulating leaf margins;
3) Large, blue violet flowers;
4) Compact habit;
5) Excellent vigor.

This new cultivar has been reproduced only by asexual propagation (division and tissue culture). Each of the progeny exhibits identical characteristics to the original plant. Asexual propagation by tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
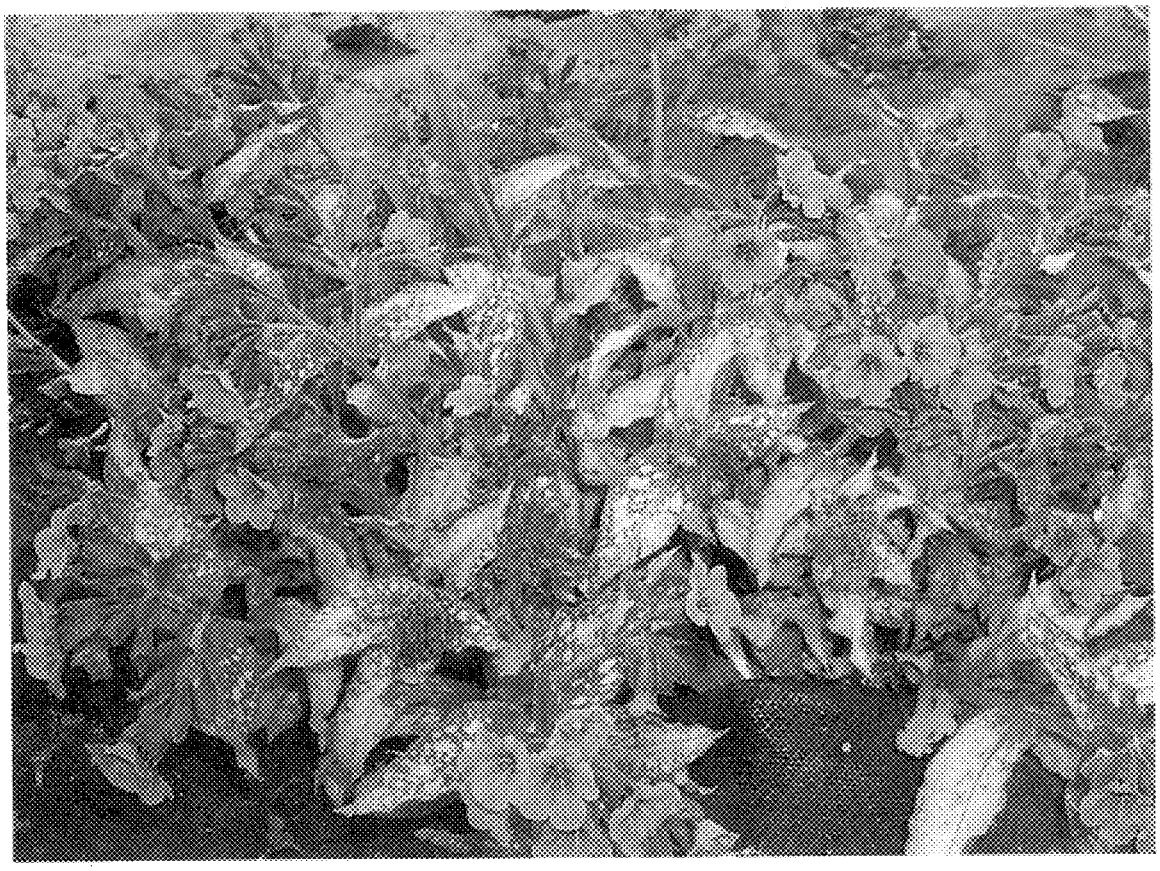
FIG. 1 shows Pulmonaria 'Silver Shimmers' in the spring growing in the ground in Canby, Oreg.
Figure 2:
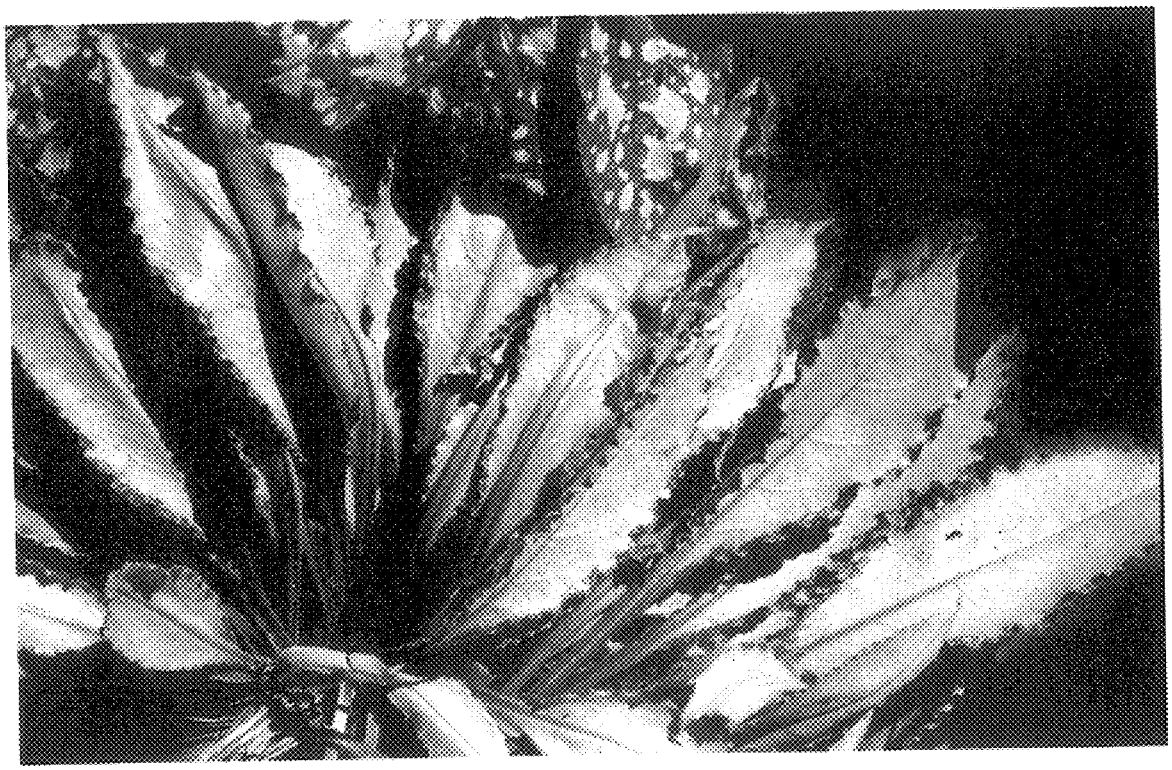
FIG. 2 shows the summer foliage.

The following is a detailed description of the new Pulmonaria hybrid based on observations of two-year-old specimens grown in the ground in Canby, Oreg. The color descriptions are all based on The Royal Horticultural Society Colour Chart.

Botanical name: Pulmonaria hybrid
Market class: Herbaceous perennial.
Plant:
- *Type.*—Herbaceous perennial.
- *Hardiness.*—USDA Zones 5 to 9.
- *Spring size.*—50 cm. wide and 25 cm. tall.
- *Summer size.*—38 cm. wide and 20 cm. tall.
- *Form.*—Basal clump.

Leaf:
- *Type.*—Simple.
- *Shape.*—Elliptic to oblanceolate.
- *Arrangement.*—Rosette.
- *Length.*—38 cm. long including petiole.
- *Width.*—8 cm. at widest.
- *Margins.*—Undulate and irregularly serrate.
- *Apex.*—Cuspidate.
- *Base.*—Attenuate.
- *Venation.*—Pinnate.
- *Texture.*—Hispid.
- *Petiole length.*—12 to 15.5 cm.
- *Petiole texture.*—Hispid.
- *Petiole color.*—Yellow Green 146A near the blade and Greyed Purple 187B near the base.
- *Color.*—Topside: Mostly silvered leaves (Greyed Green 193B) often with deep green (Green 137A) edges. Bottom: Closest to Yellow Green 147B.

Cauline leaves (These are found in the spring only on the flowering stems. After the seed is produced these stems die out.):
- *Type.*—Simple.
- *Arrangement.*—Alternate.
- *Shape.*—Variable. Elliptic, obovate, or ovate.
- *Length.*—6.7 cm.
- *Width.*—2.5 cm.
- *Margins.*—Undulate.
- *Apex.*—Acuminate.
- *Base.*—Clasping, sessile.
- *Leaf texture.*—Hispid.

*Venation.*—Pinnate.

*Color.*—Topside: Deep green, Green 137B with ¾ of the leaf covered with silver blotches, Greyed Green 193B. Bottom side: Closest to 191A.

Inflorescence:

*Type.*—Terminal forked cyme.

*Number of flowers per cyme.*—14.

*Peduncle.*—Height: 20 to 29 cm. Diameter: 3.5 cm. Texture: Hispid. Color: Yellow Green 146C.

*Pedicel.*—Length: Varies. Grows to 1.2 cm. Texture: Hispid. Color: Yellow Green 146C with Brown 200A in high light.

Flower bud:

*Size.*—1.8 cm. long and 0.5 cm. wide.

*Shape.*—Ovoid, with 7 mm exposed from the calyx.

*Color.*—Red Purple 59B.

Flower:

*Type.*—Actinomorphic.

*Shape.*—Funnelform with limbs flared our at right angles to the tube.

*Size.*—2 cm. deep and 2 to 2.4 cm. wide.

*Corolla.*—5 fused petals with rounded lobes.

*Color.*—Changes with age from rose, Red Purple 70B or 70A in the newly opened flowers, to Violet 87B to Blue Violet 94A in the mature flowers.

*Calyx.*—5 fused sepals, tubular campanulate, parted ⅓ to base, hispid.

*Calyx size.*—1.4 cm deep and 0.6 cm wide (lobes 0.3 to 0.4 cm long).

*Calyx color.*—Yellow Green 147A with a Brown 200A blush in the sun.

*Pistil.*—1.4 cm., pin type, exerted from corolla tube.

*Ovary position.*—Partly inferior.

*Carpel number.*—4.

*Stamen number.*—5, attached to and inserted in the tube.

*Pollen color.*—White 155A.

*Bloom period.*—Late February to late April in Canby, Oreg.

*Fragrance.*—None.

Seed:

*Type.*—4 smooth nutlets, Black 202A and shiny, typical of the genus.

*Fertility.*—Low.

Disease: None observed on plant grown under commercial conditions in Canby, Oreg.

Comparisons to similar Pulmonaria

Compared to Pulmonaria 'Excalibur', (U.S. Plant Pat. No. 8,958), Pulmonaria 'Silver Shimmers' has much larger, bluer flowers and undulating leaf margins.

Compared to Pulmonaria 'Silver Streamers' (U.S. Plant Pat. No. 12,135), this new cultivar has much larger, bluer flowers and more green on the leaf margins.

I claim:

1. A new and distinct hybrid of Pulmonaria plant substantially as shown and described, characterized by silver leaves with undulate margins and large, blue violet flowers.

* * * * *